US008313238B2

(12) United States Patent
Takahashi

(10) Patent No.: US 8,313,238 B2
(45) Date of Patent: Nov. 20, 2012

(54) X-RAY IMAGING DEVICE, METHOD FOR DETECTING DEVIATION OF FLAT PANEL DETECTOR, AND PROGRAM FOR THE SAME

(75) Inventor: Shoji Takahashi, Kanagawa (JP)

(73) Assignee: Fujifilm Corporation, Tokyo (JP)

(*) Notice: Subject to any disclaimer, the term of this patent is extended or adjusted under 35 U.S.C. 154(b) by 263 days.

(21) Appl. No.: 12/805,061

(22) Filed: Jul. 9, 2010

(65) Prior Publication Data
US 2011/0013752 A1    Jan. 20, 2011

(30) Foreign Application Priority Data
Jul. 15, 2009    (JP) .................................. 2009-166889

(51) Int. Cl.
*A61B 6/08*    (2006.01)
(52) U.S. Cl. ...................................... 378/205; 378/207
(58) Field of Classification Search .................. 378/205, 378/207
See application file for complete search history.

(56) References Cited

U.S. PATENT DOCUMENTS

| 4,228,420 A * | 10/1980 | Fenimore et al. ............. 382/324 |
| 2006/0280293 A1* | 12/2006 | Hardesty ....................... 378/205 |
| 2008/0112541 A1* | 5/2008 | Hardesty ....................... 378/205 |

FOREIGN PATENT DOCUMENTS
JP    2006-122488    5/2006
* cited by examiner

*Primary Examiner* — Hoon Song
(74) *Attorney, Agent, or Firm* — Jean C. Edwards, Esq.; Edwards Neils PLLC

(57) ABSTRACT

An X-ray imaging device includes an X-ray generator, a filter plate detachably attached to an X-ray outlet of the X-ray generator, and a FPD. The filter plate has a plurality of circular markers of different sizes. The smallest marker is disposed at the center of the filter plate. The other markers are disposed on lines radiating from the smallest marker in increasing order of size and at regular intervals. An X-ray radiation beam passes through the markers and patient's body, and is incident upon an imaging surface of the FPD. The FPD produces a preliminary radiographic image from the incident X-ray radiation beam. A deviation vector detector chooses adjoining two marker images of different sizes from the preliminary radiographic image, and identifies to which markers the marker images correspond based on a size ratio. Then, the deviation vector detector determines the center of an X-ray field.

18 Claims, 14 Drawing Sheets

ND METHOD FOR
X-RAY IMAGING DEVICE, METHOD FOR DETECTING DEVIATION OF FLAT PANEL DETECTOR, AND PROGRAM FOR THE SAME

CROSS-REFERENCE TO RELATED APPLICATIONS

The present application claims priority from Japanese Patent Application No. 2009-166889, filed Jul. 15, 2009, the contents of which are herein incorporated by reference in their entirety.

BACKGROUND OF THE INVENTION

1. Field of the Invention

The present invention relates to an X-ray imaging device using a flat panel detector (FPD), a method, and a program for detecting deviation between the FPD and an X-ray field.

2. Description Related to the Prior Art

Digital radiography using a flat panel detector (FPD) for X-ray imaging has come into widespread use in a medical field in recent years. The FPD has small size, light weight, and a large imaging surface. In an X-ray imaging device having the FPD, an X-ray radiation beam produced by an X-ray generator is applied to patient's body part to be viewed. The X-ray radiation beam passes through the body part of the patient, and the FPD captures the X-ray radiation beam behind the body part. The FPD produces a digital-format radiographic image from the captured X-ray radiation beam. The FPD can immediately apply image processing or enhancement to the radiographic image because the radiographic image is in the digital format. The radiographic image is directly displayed on a monitor. The FPD allows immediate display of the radiographic image on the monitor, without development of an exposed film in a darkroom or read of an imaging plate (IP) with a laser scanner, as conventionally.

The X-ray generator is provided with a collimator unit. The collimator unit has openable and closable collimator leaves that make an X-ray field of the X-ray radiation beam into a rectangular shape, similarly to the imaging surface of the FPD, before the application to patient's body. The collimator leaves cut redundant X-rays from the X-ray radiation beam, and reduce unnecessary X-ray radiation absorption by the patient's body.

It is desirable that the center of the X-ray field formed by the collimator leaves coincide with the center of the imaging surface of the FPD. However, the position of the FPD relative to the X-ray generator is visually checked and adjusted by a radiological technologist, and adjustment accuracy depends on skill of the technologist. Accordingly, it is proposed to capture a preliminary radiographic image for the position adjustment before capturing a diagnostic radiographic image, for the purpose of quantitatively detecting deviation between the imaging surface of the FPD and the X-ray field.

Taking a case of an X-ray imaging device according to Japanese Patent Laid-Open Publication No. 2006-122488 as an example, an image of the rectangular X-ray field is captured. Then, X-directional midpoint coordinates and Y-directional midpoint coordinates of the X-ray field are obtained from the image, to detect the center of the X-ray field.

In this method, however, the whole X-ray field has to be seen in the image to obtain the X-directional midpoint coordinates and the Y-directional midpoint coordinates. Thus, if a part of the X-ray field lies off the imaging surface due to large deviation, the center of the X-ray field is undetectable.

Especially, a portable FPD called as an electronic cassette is disposed between a bed and the patient lying thereon to capture a radiographic image. The FPD is repositioned whenever capturing the image, in accordance with a body size of the patient or the body part to be viewed. The reposition of the FPD tends to cause deviation of the imaging surface of the FPD from the X-ray field.

SUMMARY OF THE INVENTION

An object of the present invention is to provide an X-ray imaging device, a method, and a program that can detect the amount of deviation between an imaging surface of a flat panel detector (FPD) and an X-ray field, even if the deviation is large.

An X-ray imaging device according to the present invention includes an X-ray generator for applying an X-ray radiation beam to an object to be viewed, a position detection pattern disposed between the X-ray generator and the object to be viewed, a flat panel detector (FPD) disposed behind the object to be viewed, and a deviation vector detector. The X-ray radiation beam partly passes through the position detection pattern and the object to be viewed, and is incident upon an imaging surface of the FPD. The FPD produces a preliminary radiographic image from the incident X-ray radiation beam. The deviation vector detector determines the center of an X-ray field of the X-ray radiation beam from the preliminary radiographic image, and calculates a deviation vector extending from the center of the X-ray field to the center of the imaging surface of the FPD.

The position detection pattern includes a plurality of markers. The markers are laid out in such a manner that marker images formed by the X-ray radiation beam that has passed through the markers are disposed radially from the center of the X-ray field in the preliminary radiographic image.

The markers are preferably laid out on the position detection pattern in such a manner that the marker images having different characteristic values are disposed radially from the center of the X-ray field, and the marker images having the same characteristic value are disposed at a same distance from the center of the X-ray field. The deviation vector detector determines the center of the X-ray field from two of the marker images that have the different characteristic values and a shortest center-to-center distance.

The position detection pattern may be a filter plate having holes as the markers. The filter plate may be detachably attached to an X-ray outlet of the X-ray generator. Otherwise, the position detection pattern may be a collimator leaf having holes as the markers.

The markers may have a circular shape, and the characteristic value of the marker image may be its size. The deviation vector detector determines the center of the X-ray field based on the ratio in size between the two marker images adjoining to each other.

The markers may have various polygonal shapes, and the characteristic value of the marker image may be its shape. The deviation vector detector determines the center of the X-ray field based on the shapes of the two marker images adjoining to each other.

It is preferable that the X-ray imaging device further include at least one of a rotation angle detector, an orthogonality detector, and a source-to-image distance detector. The rotation angle detector detects a rotation angle of the imaging surface of the FPD relative to the X-ray field of the X-ray radiation beam from the center of the X-ray field determined by the deviation vector detector and one of the marker images, or from two of the marker images. The orthogonality detector detects orthogonality of the imaging surface of the FPD relative to the central ray of the X-ray radiation beam, on the basis of difference in shape between the single marker and the marker image corresponding to the single marker. The source-to-image distance detector detects a source-to-image distance from an X-ray focus of the X-ray generator to the imaging surface of the FPD, on the basis of the ratio in size between the single marker and the marker image corresponding to the single marker.

The position detection pattern may be a filter plate having a plurality of areas with different X-ray transmittances as the markers. The filter plate is detachably attached to the X-ray outlet of the X-ray generator. A plurality of marker images that are produced from the X-ray radiation beam having passed through the areas have X-ray densities different from one another as characteristic values. The deviation vector detector determines the center of the X-ray field on the basis of the ratio in the X-ray density between the two marker images.

The position detection pattern may be an openable and closable collimator leaf. The preliminary radiographic image may be obtained with a software program for synchronously controlling the intensity of the X-ray radiation beam emitted from the X-ray generator and a degree of opening of the collimator leaf.

It is preferable that in capturing the preliminary radiographic image, the X-ray generator be supplied with a voltage lower than that in capturing a diagnostic radiographic image, so as to generate the X-ray radiation beam of intensity lower than that in capturing the diagnostic radiographic image.

A method for detecting a deviation of a FPD includes the steps of generating an X-ray radiation beam of low intensity from an X-ray generator, passing the X-ray radiation beam through a position detection pattern and an object to be viewed, and applying the passed X-ray radiation beam to an imaging surface of a FPD, generating a preliminary radiographic image from the applied X-ray radiation beam, determining a center of an X-ray field of the X-ray radiation beam from the preliminary radiographic image, and calculating a deviation vector extending from the center of the X-ray field to a center of the imaging surface of the FPD.

The center of the X-ray field of the X-ray radiation beam may be determined by extrapolation.

The method preferably further includes at least one of the steps of detecting a rotation angle of the imaging surface of the FPD relative to the X-ray field of the X-ray radiation beam from the preliminary radiographic image, detecting orthogonality of the imaging surface of the FPD relative to a central ray of X-ray radiation beam from the preliminary radiographic image, and detecting a source-to-image distance from an X-ray focus of the X-ray generator to the imaging surface of the FPD from the preliminary radiographic image.

At least one of the deviation vector, the rotation angle, the orthogonality, and the source-to-image distance may be displayed on a monitor.

A storage medium having stored thereon a computer program executable to perform the steps of generating an X-ray radiation beam of low intensity from an X-ray generator, passing the X-ray radiation beam through a position detection pattern and an object to be viewed, and applying the passed X-ray radiation beam to an imaging surface of a FPD, generating a preliminary radiographic image from the applied X-ray radiation beam, determining the center of an X-ray field of the X-ray radiation beam from the preliminary radiographic image, and calculating a deviation vector extending from the center of the X-ray field to the center of the imaging surface of the FPD.

According to the present invention, the predetermined patterned images for position detection are formed on the imaging surface of the FPD, and the patterned images of the preliminary radiographic image outputted from the FPD are analyzed to determine the center of the X-ray field. Thus, it is possible to precisely detect a deviation amount, even if the imaging surface of the FPD significantly deviates from the X-ray field so that the center of the X-ray field is out of the imaging surface.

BRIEF DESCRIPTION OF THE DRAWINGS

For more complete understanding of the present invention, and the advantage thereof, reference is now made to the following descriptions taken in conjunction with the accompanying drawings, in which.

DESCRIPTION OF THE PREFERRED EMBODIMENTS

First Embodiment

Figure 1:
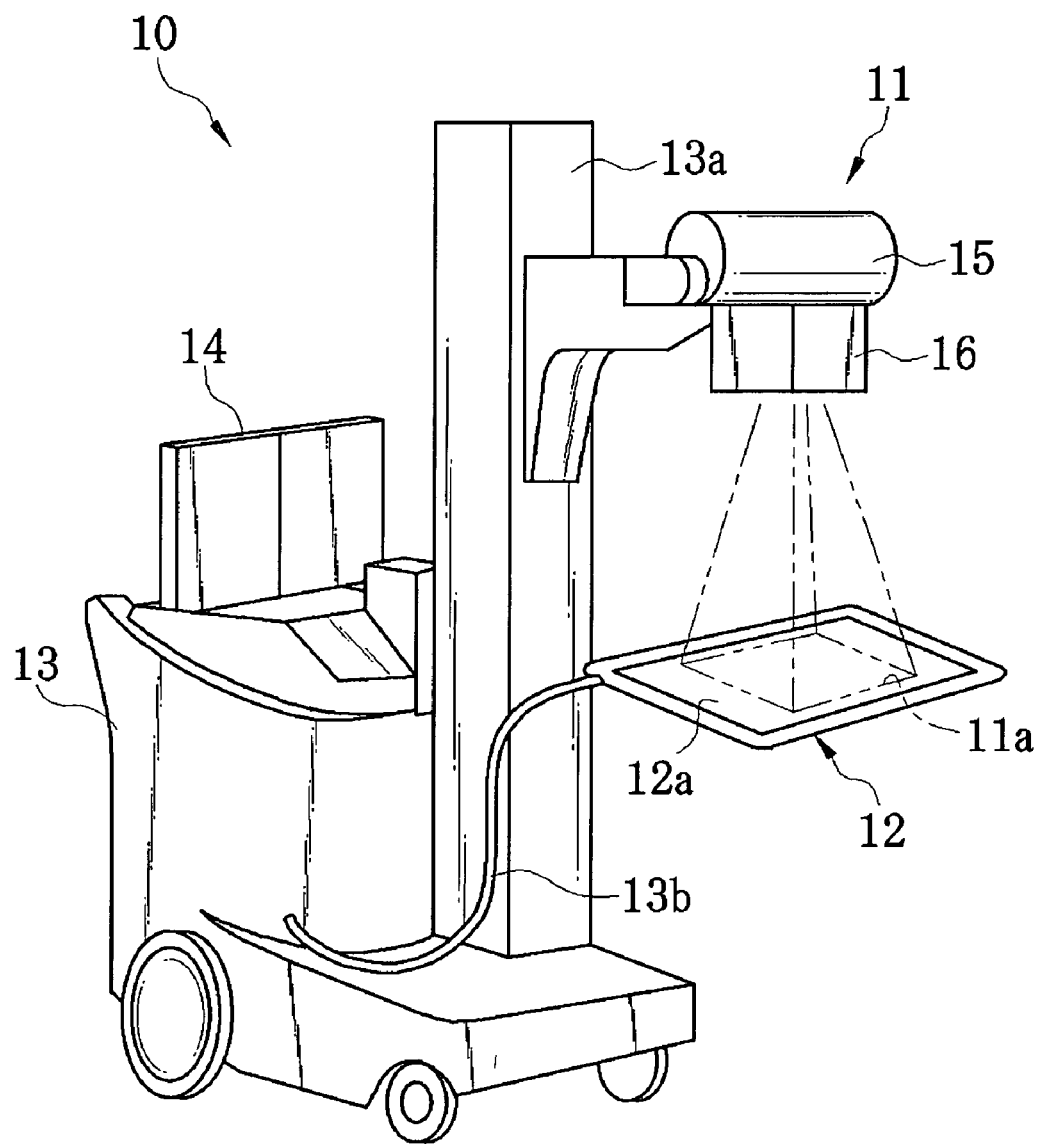
FIG. 1 is a perspective view of an X-ray imaging device according to a first embodiment.

As shown in FIG. 1, an X-ray imaging device 10 is formed integrally with a cart or a wagon in a movable manner. The X-ray imaging device 10 is constituted of an X-ray generator 11, a portable flat panel detector (FPD) 12 called as an electronic cassette, a main body 13 integrally attached to the cart, and a monitor 14 attached to the main body 13. The X-ray generator 11 is slidably attached to a column 13a, and emits an X-ray radiation beam as shown by chain double-dashed lines of FIG. 1. The emitted X-ray radiation beam passes through patient's body, and then the FPD 12 receives the X-ray radiation beam to produce a radiographic image. The FPD 12 is connected to the main body 13 through a cable 13b.

On the monitor 14, which is a liquid crystal display, the radiographic image outputted from the FPD 12, a GUI (graphical user interface) image, and the like are displayed.

Figure 2:
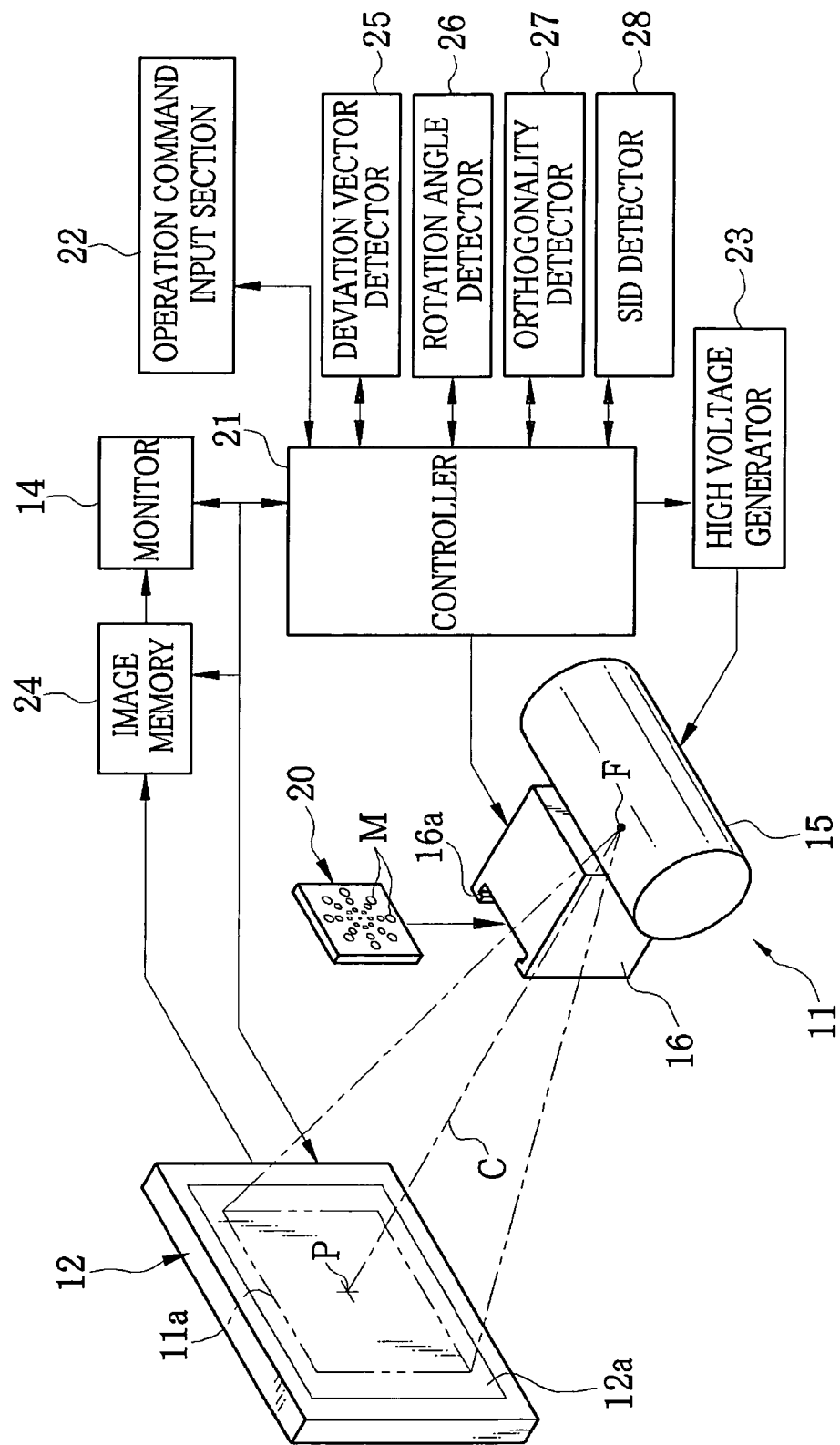
FIG. 2 is a block diagram showing the electrical structure of the X-ray imaging device and the schematic structure of an X-ray generator and a FPD.

The main body 13 contains a controller 21 (see FIG. 2). The controller 21 controls the operation of the X-ray imaging device 10, including emission of the X-ray radiation beam by the X-ray generator 11 and reception of the X-ray radiation beam by the FPD 12, based on commands inputted from an operation command input section 22 (see FIG. 2) including a key board, a mouse, a foot pedal, and the like provided to the main body 13. From the operation command input section 22, imaging conditions are setup, and a preliminary radiographic image capture command for detecting deviation of the FPD 12 and a diagnostic radiographic image capture command are inputted.

The X-ray generator 11 is constituted of an X-ray tube 15 for emitting the X-ray radiation beam, and a collimator unit 16 having a plurality of collimator leaves. The X-ray radiation beam emitted from the X-ray tube 15 is partly cut out by the collimator unit 16 so as to have a rectangular X-ray field 11a. Then, the X-ray radiation beam is applied to a body part of the patient, and more or less absorbed according to the density and composition of the body part. The remaining X-ray radiation beam that has passed through the body part without absorption is incident upon an imaging surface 12a of the FPD 12.

The FPD 12 is an indirect conversion type of X-ray detector having a panel and a module (both are not illustrated). The panel is constituted of a phosphor layer and a detecting element layer. The module is constituted of a drive circuit for driving the detecting element layer, a signal processing circuit for converting an image signal read from the panel into digital image data. The phosphor layer contains a phosphor such as CsI (cesium iodide), and converts the incident X-ray radiation beam into visible light. The detecting element layer has a sensor matrix consisting of pixels arranged into two dimensions. Each pixel has a photodiode for converting the visible light into electric charge and accumulating the electric charge therein, and a TFT (thin film transistor) switch for controlling a flow of the electric charge accumulated in the photodiode. The FPD 12 may be a direct conversion type of X-ray detector in which a conversion layer made of amorphous selenium or the like directly converts the X-ray radiation beam into the electric charge.

The FPD 12 captures a radiographic image based on a control signal sent from the controller 21 of the main body 13 through the cable 13b, and outputs the radiographic image through the cable 13b. The FPD 12 is movable within reach of the cable 13b, and is appropriately disposed behind the body part to be viewed. The X-ray generator 11 is orthogonally slidable along the column 13a, and is horizontally rotatable within a predetermined angular range. Thus, the incident position and angle of the X-ray radiation beam are appropriately adjustable. The FPD 12 may be a radio type electronic cassette that communicates with the main body 13 by radio without using the cable 13b.

In FIG. 2, a filter attachment section 16a is formed at an X-ray outlet of the collimator unit 16. Into the filter attachment section 16a, a rectangular filter plate 20 is fitted from above orthogonally to an X-ray incident direction. The filter plate 20 is made of a material such as lead that can intercept the X-ray radiation beam. In the filter plate 20, a plurality of holes (markers) M are formed to pass a part of the X-ray radiation beam therethrough. The filter plate 20 is fitted into the filter attachment section 16a in capturing the preliminary radiographic image to check the deviation of the FPD 12, and is detached therefrom in capturing the diagnostic radiographic image.

The controller 21 has a CPU for controlling the operation of the X-ray imaging device 10, a ROM for storing programs executed by the CPU, and a RAM functioning as a work area of the CPU. In addition to the monitor 14 and the operation command input section 22, a high voltage generator 23, an image memory 24, a deviation vector detector 25, a rotation angle detector 26, an orthogonality detector 27, and a source-to-image distance (SID) detector 28, all of which are laid out on circuitry contained in the main body 13, are connected to the controller 21. The deviation vector detector 25, the rotation angle detector 26, the orthogonality detector 27, and the SID detector 28 carry out detection processing on the preliminary radiographic image, and are composed of an IC (integrated circuit), a FPGA (field programmable gate array), the CPU, and the programs stored on the ROM.

The high voltage generator 23 generates voltage under the control of the controller 21 in accordance with the intensity of the X-ray radiation beam to be generated from the X-ray tube 15 in capturing the preliminary radiographic image or the diagnostic radiographic image, and applies the generated voltage to the X-ray tube 15 through a high voltage cable. Upon the application of the voltage, the X-ray tube 15 emits the X-ray radiation beam from an X-ray focus F, which can be regarded as a point source.

The X-ray radiation beam emitted from the X-ray tube 15 is partly cut out by the collimator leaves of the collimator unit 16 so as to have the rectangular X-ray field. If the filter plate 20 is not fitted into the filter attachment section 16a, the X-ray radiation beam having the rectangular X-ray field 11a is incident upon the imaging surface 12a of the FPD 12. The size of the X-ray field 11a depends on a source-to-image distance (SID, distance from the X-ray focus F to a center P of the X-ray field 11a). If the filter plate 20 is fitted into the filter attachment section 16a, on the other hand, the X-ray radiation beam from the collimator unit 16 passes through only the markers M of the filter plate 20, and forms on the imaging surface 12a of the FPD 12 a patterned image corresponding to the shape and arrangement of the markers M. The FPD 12 captures the patterned image, and outputs the patterned image as the preliminary radiographic image. The preliminary radiographic image outputted from the FPD 12 is written to the image memory 24, and is outputted to the monitor 14 under the control of the controller 21.

Figure 3:
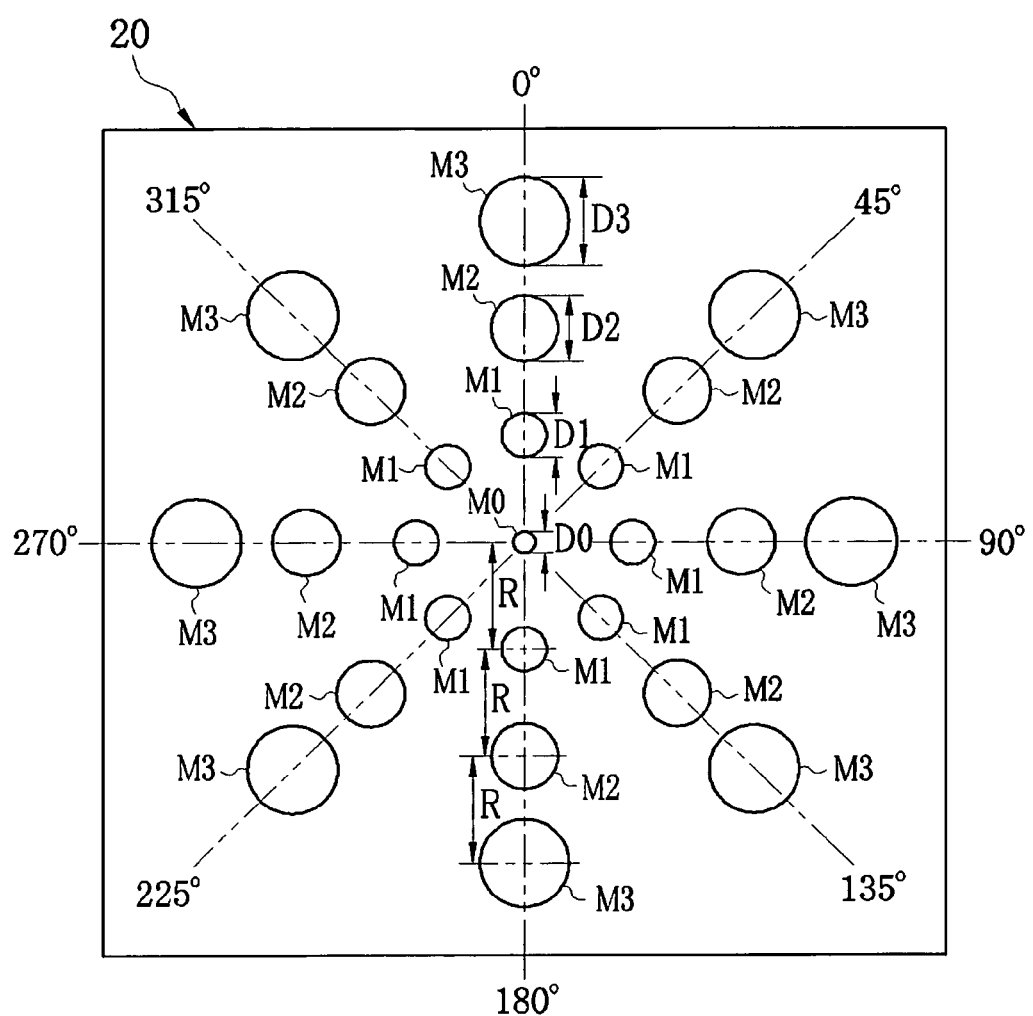
FIG. 3 is a top plan view of a filter plate.

As shown in FIG. 3, a plurality of markers M0 to M3 of different sizes are formed in the filter plate 20. All of the markers M0 to M3 are in the shape of a circle. The marker M0 is disposed at the center of the filter plate 20. The other markers M1 to M3 are disposed on lines radiating from the marker M0. The radiating lines form 0°, 45°, 90°, 135°, 180°, 225°, 270°, and 315° with a vertical center line of the filter plate 20. The markers M1 to M3 are disposed one by one on each radiating line in increasing order of size from a marker M0 side, in such a manner that the centers of the markers M1 to M3 are spaced at regular intervals R. In other words, if three concentric circles, the centers of which coincide with the center of the marker M0, have diameters of R, 2R, and 3R, the centers of the markers M1 are disposed on the concentric circle with the diameter of R. The centers of the markers M2 are disposed on the concentric circle with the diameter of 2R, and the centers of the markers M3 are disposed on the concentric circle with the diameter of 3R.

The markers M0 to M3 satisfy the following equations:

$$D1 = 2 \cdot D0$$

$$D2 = 3 \cdot D0$$

$$D3 = 4 \cdot D0$$

Wherein, D0 represents the diameter of the marker M0. D1 represents the diameter of the marker M1. D2 represents the diameter of the marker M2. D3 represents the diameter of the marker M3. Thus, the ratio of diameters between the two markers adjoining on the radiating line depends on which markers to be chosen as follows:

The ratio of diameters between the markers M0 and M1: D1/D0=2

The ratio of diameters between the markers M1 and M2: D2/D1=3/2

The ratio of diameters between the markers M2 and M3: D3/D2=4/3

The filter plate 20 having these markers M0 to M3 is fitted into the filter attachment section 16a, in such a manner that surfaces of the filter plate 20 are orthogonal to a central ray C of the X-ray radiation beam from the collimator unit 16, and the center of the marker M0 coincides with the central ray C.

The deviation vector detector 25 identifies the center P of the X-ray field 11a based on images of the markers M0 to M3 (hereinafter called marker images) in the preliminary radiographic image, which is captured in a state of the filter plate 20 being fitted into the filter attachment section 16a. Then, the deviation vector detector 25 determines a deviation vector V that represents a deviation amount and a deviation direction from the center P of the X-ray field 11a to a center Q of the imaging surface 12a of the FPD 12.

Figure 4:
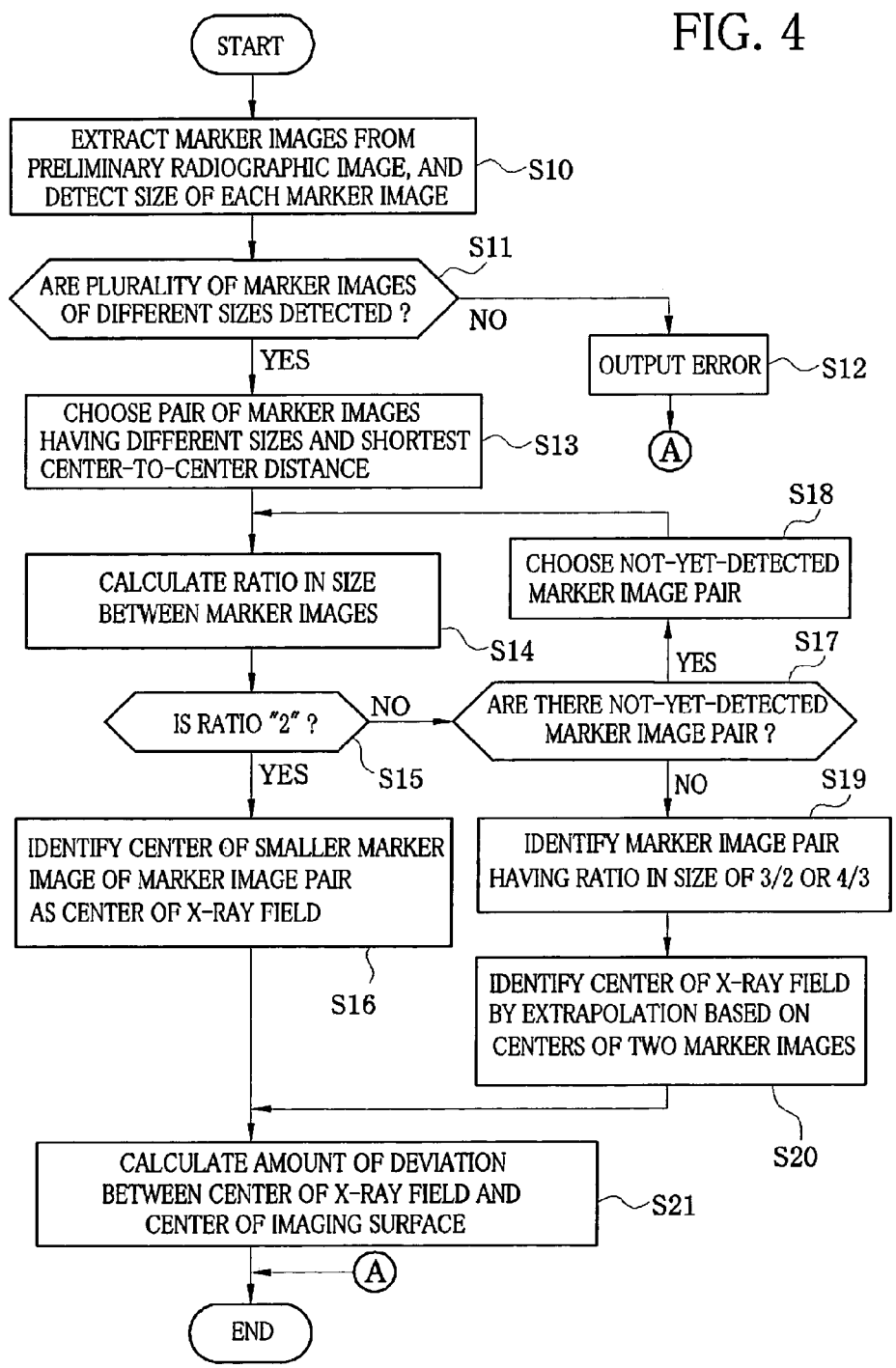
FIG. 4 is a flowchart of the operation of a deviation vector detector.

To be more specific, the deviation vector detector 25 carries out operation according to a flowchart of FIG. 4. The deviation vector detector 25 first extracts the marker images from the preliminary radiographic image, and detects the size of each marker image (S10). If the imaging surface 12a of the FPD 12 is orthogonal to the central ray C of the X-ray radiation beam, the marker image has a circular shape. In this case, the diameter of the circle becomes the size of the marker image. The size of the marker image is expressed in pixels, for example. On the other hand, if the imaging surface 12a of the FPD 12 is not orthogonal, namely is inclined to the central ray C, the marker image has an oval shape. In this case, the length of the minor axis of the oval becomes the size of the marker image. This is because the length of the minor axis of the oval is substantially equal to the diameter of the circle of the marker image in the orthogonal case. The deviation vector detector 25 extracts the circles or ovals from the preliminary radiographic image with use of a commonly known template matching technique.

Then, the deviation vector detector 25 judges whether or not a plurality of marker images of different sizes are detected in S10 (S11). If only the single marker image or marker images of same size is/are detected (NO in S11), the center P of the X-ray field 11a is undetectable in the following steps. Thus, the deviation vector detector 25 outputs an error to the controller 21 (S12), and ends the operation. If YES in S11, the deviation vector detector 25 chooses a pair of marker images that have different sizes and the shortest center-to-center distance, among the detected marker images (S13).

Figure 5:
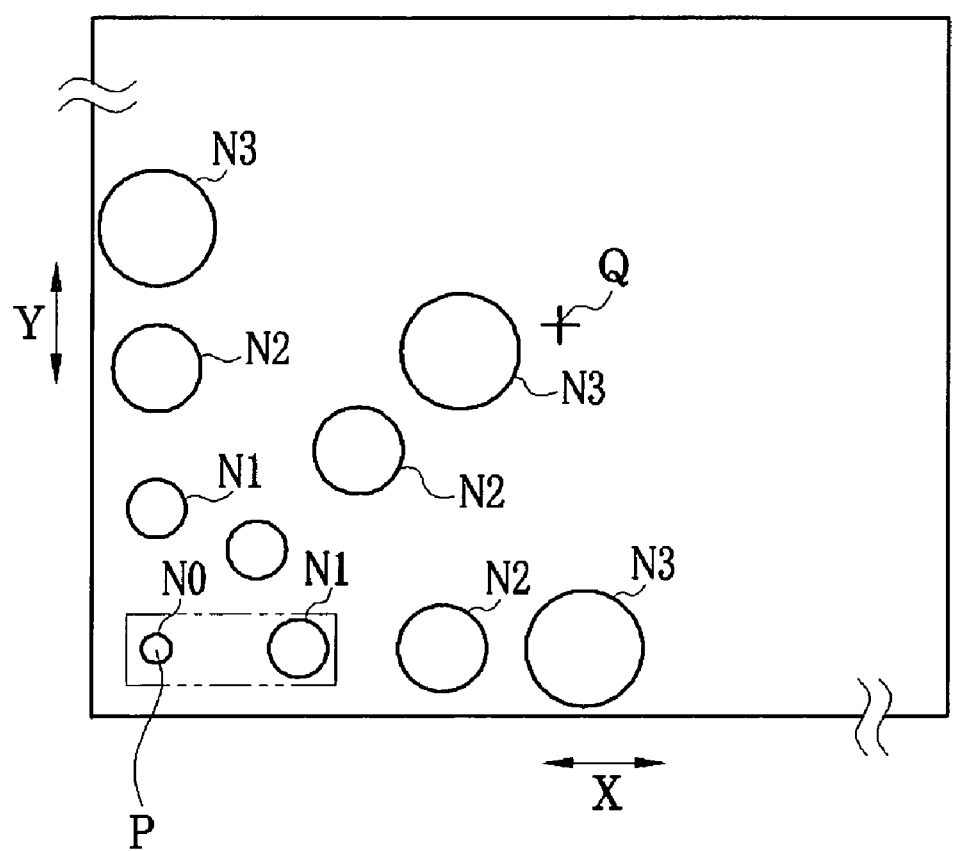
FIG. 5 is an explanatory view of an example of a preliminary radiographic image.

Taking a case where the preliminary radiographic image shown in FIG. 5 is obtained in S10 as an example, there are a plurality of marker image pairs to be chosen. The deviation vector detector 25 chooses the single marker image pair in predetermined order, e. g. in increasing order of size. In FIG. 5, marker images N0 to N3 correspond to the markers M0 to M3. If a pair of marker images N0 and N1 that adjoin to each other in an X direction are chosen, the center of the marker image N0 coincides with the center P of the X-ray field 11a. The ratio of size between the marker images N0 and N1 (size of the marker image N1/size of the marker image N0) is equal to the ratio of size between the markers M0 and M1, and approximately "2". As a matter of course, it is not yet specified to which one of the markers M0 to M3 each of the marker images N0 to N3 in the preliminary radiographic image corresponds, at the time of S13.

Next, the deviation vector detector 25 calculates the ratio of size between the two marker images M0 and M1 (the diameters of the circles or the lengths of the minor axes of the ovals) chosen in S13 (S14). The ratio is calculated by dividing the size of the larger marker image by the size of the smaller marker image. Then, the deviation vector detector 25 judges whether or not the ratio calculated in S14 is "2" (S15). If YES in S15, it turns out that the chosen marker image pair include the marker images N0 and N1. Thus, the deviation vector detector 25 identifies the center of the smaller marker image N0 as the center P of the X-ray field 11a (S16).

If N0 in S15, on the other hand, the deviation vector detector 25 judges whether or not there are a not-yet-detected marker image pair in the preliminary radiographic image (S17). If YES in S17, the not-yet-detected marker image pair are chosen (S18), and the operation returns to S14.

If N0 in S17, the deviation vector detector 25 judges that no marker image N0 exists in the preliminary radiographic image. In this case, the deviation vector detector 25 identifies the marker image pair having a ratio of "3/2" or "4/3", based on a calculation result of S14 (S19). The ratio of "3/2" corresponds to the marker image pair including the marker images N1 and N2, and the ratio of "4/3" corresponds to the marker image pair including the marker images N2 and N3.

Figure 6:
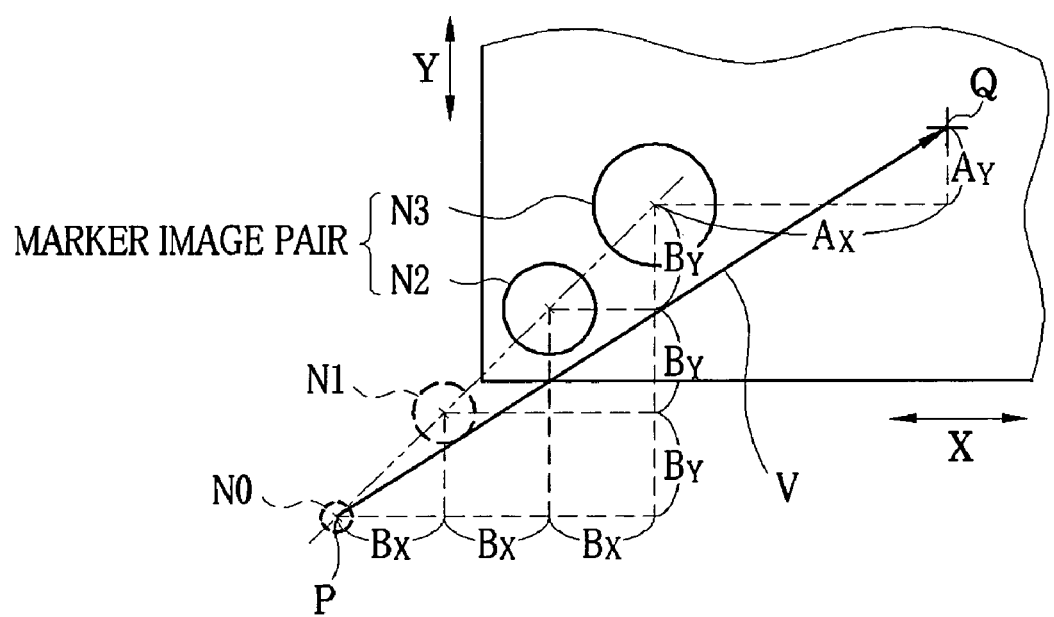
FIG. 6 is an explanatory view of a calculation method of a deviation vector.

Then, the deviation vector detector 25 determines the center P of the X-ray field 11a (the center of the marker image N0) based on the centers of the two marker images identified in S19 by extrapolation (a method to logically estimate a value outside a known range from values within the known range) (S20). To be more specific, the deviation vector detector 25 identifies that the chosen marker image pair include the marker images N1 and N2 or the marker images N2 and N3 based on the ratio in size between the two marker images. Considering that the identified two marker images N1 and N2, or N2 and N3 are positioned on the line radiating from the marker image N0, and the centers of the marker images N0 to N3 are spaced uniformly, the center of the marker image N0, that is, the center P of the X-ray field 11a is determined by extrapolation. FIG. 6 shows an example of determining the center P of the X-ray field 11a by extrapolation, based on the marker image pair including the marker images N2 and N3.

As shown in FIG. 6, an X direction refers to a horizontal direction of the imaging surface 12a, and a Y direction refers to a vertical direction thereof. The deviation vector detector 25 calculates the deviation between the center P of the X-ray field 11a determined in S16 or S20 and the center Q of the imaging surface 12a (the center of the preliminary radiographic image) as a deviation vector V in the X and Y coordinates of the imaging surface 12a, and outputs the deviation vector V to the controller 21 (S21). As described above, even if the FPD 12 significantly deviates from the X-ray field 11a, and no marker image N0 exists in the preliminary radiographic image, the deviation vector detector 25 can detect the position of the center P of the X-ray field 11a, and determine the deviation vector V.

How to determine the deviation vector V, which is from the center P of the X-ray field 11a to the center Q of the imaging surface 12a, will be concretely described with referring to FIG. 6. The deviation vector detector 25 firstly calculates X and Y components $(A_X, A_Y)$ of a vector A from the center of the marker image N3 to the center Q of the imaging surface 12a, and XY components $(B_X, B_Y)$ of a vector B from the center of the marker image N2 to the center of the marker image N3, based on the preliminary radiographic image. Since it is apparent from the ratio in size between the marker images N3 and N2 that the marker image N3 corresponds to the third marker M3 from the marker M0, the X and Y components ($B_X$, $B_Y$) of the vector B are tripled to calculate X and Y components ($3B_X$, $3B_Y$) of a vector B' from the center P of the X-ray field 11a to the center of the marker image N3. The sum of the vectors A and B' becomes the deviation vector V, and hence X and Y components of the deviation vector V are represented by ($A_X+3B_X$, $A_Y+3B_Y$).

The X and Y components ($A_X+3B_X$, $A_Y+3B_Y$) of the deviation vector V are expressed in pixels in the preliminary radiographic image. Thus, the amount of deviation (X, Y) in real space from the center P of the X-ray field 11a to the center Q of the imaging surface 12a is represented by ($p \times (A_X+3B_X)$, $p \times (A_Y+3B_Y)$), wherein p represents a pixel pitch in the imaging surface 12a.

Figure 7:
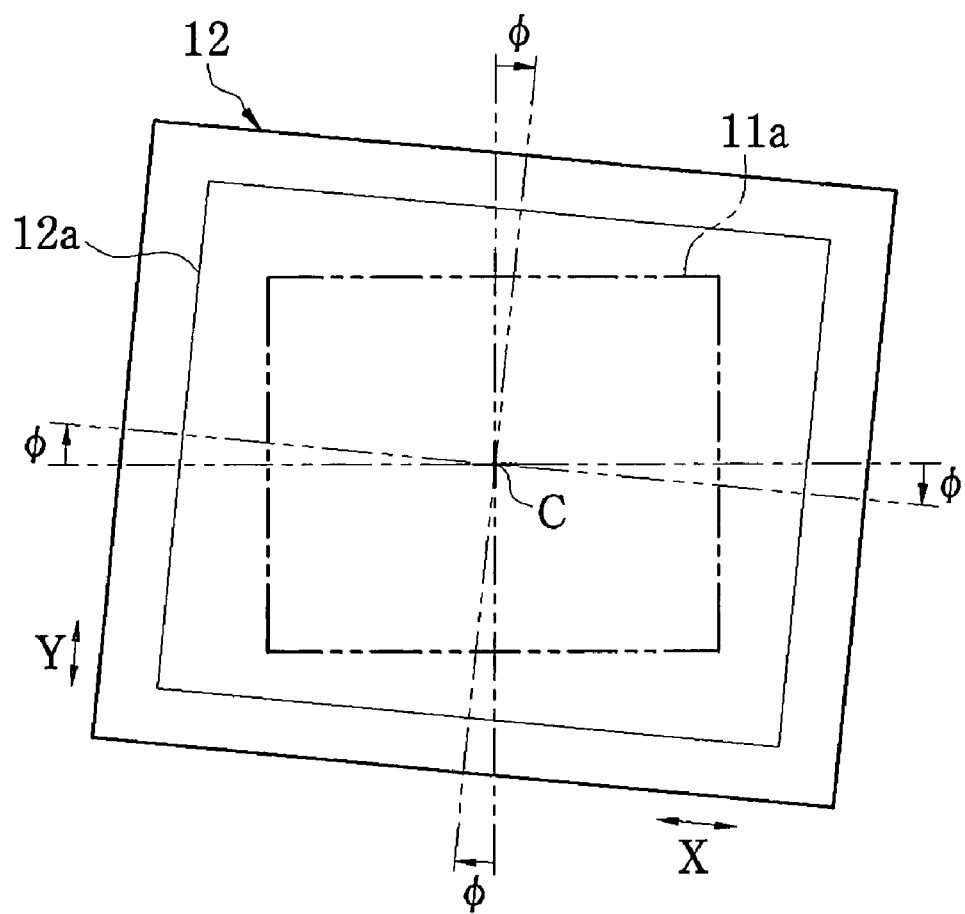
FIG. 7 is a top plan view of a FPD disposed at an angle with respect to an X-ray field.

The rotation angle detector 26 detects a rotation angle of the imaging surface 12a of the FPD 12 relative to the X-ray field 11a, with the use of a detection result of the marker images N0 to N3 by the deviation vector detector 25. To be more specific, as shown in FIG. 7, the rotation angle detector 26 detects a rotation angle φ of the imaging surface 12a in a clockwise direction around the central ray C of the X-ray radiation beam. In FIG. 6, the deviation vector detector 25 detects the marker images N2 and N3, and identifies at least one line on which the marker images N0 to N3 are orderly arranged. The rotation angle detector 26 calculates an angle that the identified line forms with a vertical center line of the imaging surface 12a, and finds out to which of reference angles 0°, 45°, 90°, 135°, 180°, 225°, 270°, and 315° the calculated angle is nearest. The rotation angle detector 26 calculates the rotation angle φ from difference between the calculated angle and the reference angle, and outputs the rotation angle φ to the controller 21.

The orthogonality detector 27 detects the orthogonality between the central ray C of the X-ray radiation beam and the imaging surface 12a of the FPD 12. To be more specific, the orthogonality detector 27 calculates inclination angles $\theta_X$ and $\theta_Y$ of the imaging surface 12a around X and Y axes orthogonal to the central ray C, with respect to a case that the imaging surface 12a is orthogonal to the central ray C, based on the shape of the marker image detected by the deviation vector detector 25. The calculated inclination angles $\theta_X$ and $\theta_Y$ are outputted to the controller 21 by the orthogonality detector 27.

Figure 8A:
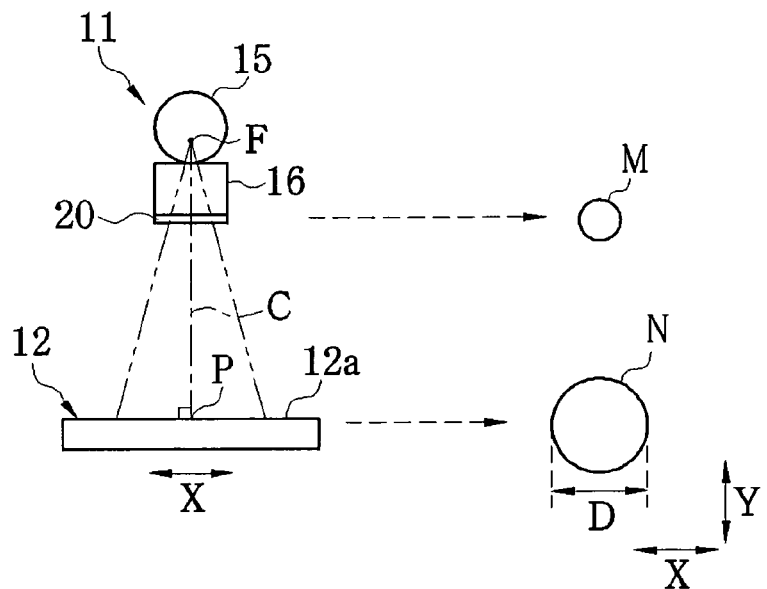
FIG. 8A is an explanatory view showing the shape of a marker image in a case where an imaging surface is orthogonal to the central ray of an X-ray radiation beam.
Figure 8B:
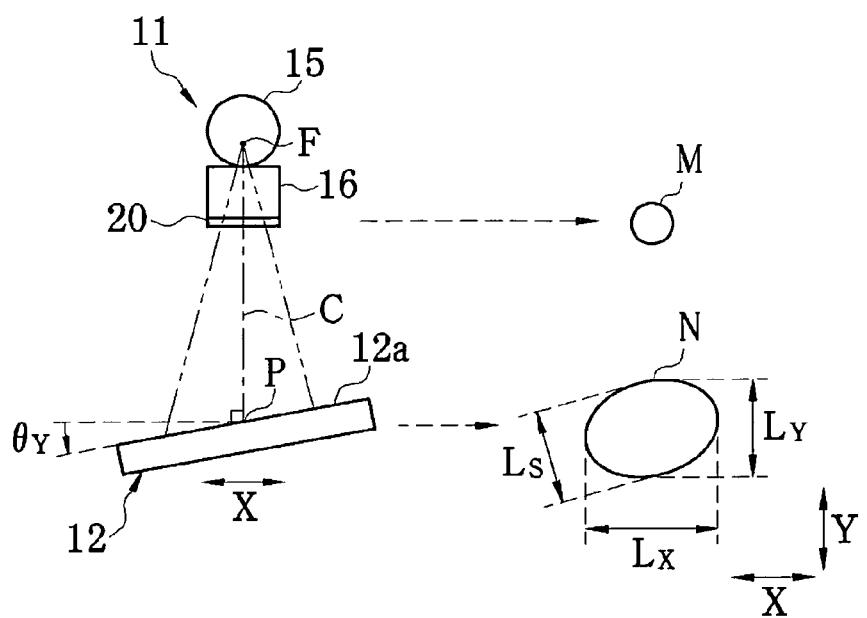
FIG. 8B is an explanatory view showing the shape of a marker image in a case where the imaging surface is not orthogonal to the central ray of the X-ray radiation beam.

If the imaging surface 12a is orthogonal to the central ray C, as shown in FIG. 8A, the marker image is in the shape of a circle similar to the shape of the marker. On the other hand, if the imaging surface 12a is inclined relative to the central ray C, as shown in FIG. 8B, the marker image is in the shape of an oval. The orthogonality detector 27 focuses attention on one of the marker images detected by the deviation vector detector 25. If the marker image has the circular shape, the orthogonality detector 27 judges that both of the inclination angles $\theta_X$ and $\theta_Y$ of the imaging surface 12a are equally zero ($\theta_X=\theta_Y=0$). If the marker image has the oval shape, the orthogonality detector 27 calculates the inclination angles $\theta_X$ and $\theta_Y$ by the following expressions (1) and (2).

$$\theta_X = \cos^{-1}(L_S/L_Y) \quad (1)$$

$$\theta_Y = \cos^{-1}(L_S/L_X) \quad (2)$$

Wherein, $L_X$ represents the length of the oval marker image in the X direction, and $L_Y$ represents the length of the oval marker image in the Y direction. $L_S$ represents the length of the minor axis of the oval marker image. The length $L_S$ of the minor axis is substantially equal to the diameter D of the circular marker image in a case where the imaging surface 12a is not inclined (the case of FIG. 8A).

Figure 9:
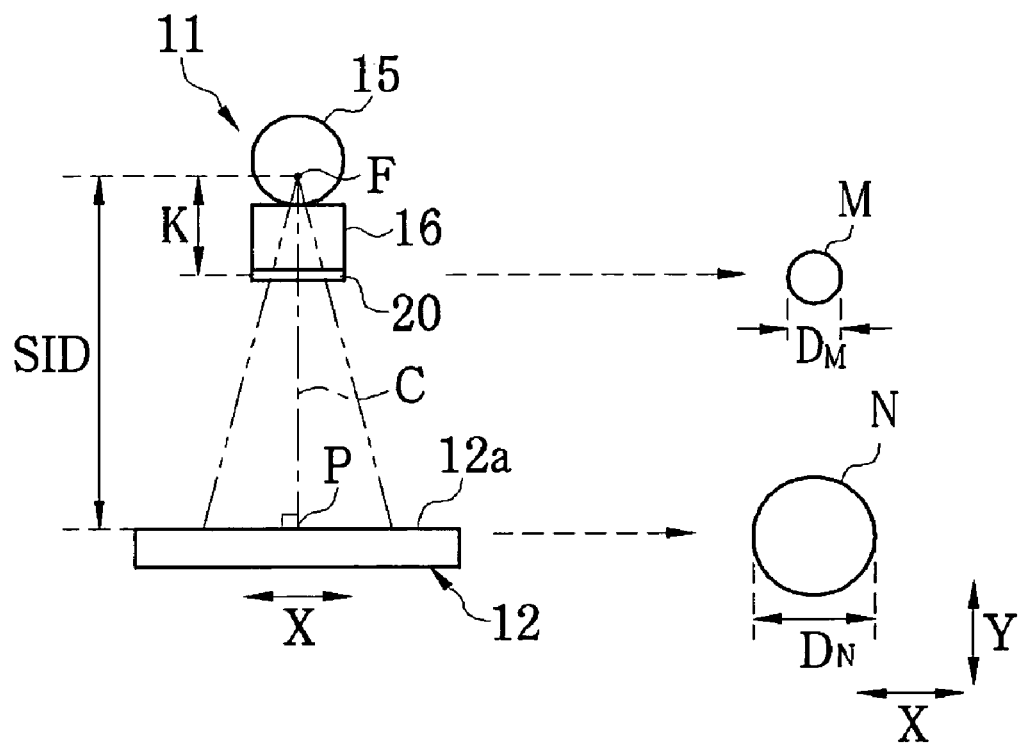
FIG. 9 is an explanatory view showing how to calculate a SID (source-to-image distance)

The SID detector 28, as shown in FIG. 9, detects source-to-image distance (SID) from the X-ray focus F to the center P of the X-ray field 11a, by using the detection result of the marker image by the deviation vector detector 25. To be more specific, the SID detector 28 calculates the SID by the following expression (3), considering that the ratio of size between the marker and the corresponding marker image is proportional to the SID.

$$SID = (K/D_M) \times D_N \quad (3)$$

Wherein, K represents distance from the X-ray focus F to the filter plate 20. $D_M$ represents the diameter of the marker, and $D_N$ represents the diameter of the marker image in a case where the marker image has the circular shape. The distance K and the diameter $D_M$ of the marker are fixable with design of the X-ray generator 11 and the filter plate 20, and these values are stored in advance on the ROM in the controller 21. The SID is calculated by using the diameter $D_N$ of the marker image as a parameter. If the imaging surface 12a is inclined relative to the central ray C, the marker image has the oval shape. Thus, the SID detector 28 calculates the SID with use of the length $L_S$ of the minor axis of the oval marker image, instead of the diameter $D_N$ of the circular marker image.

Figure 10:
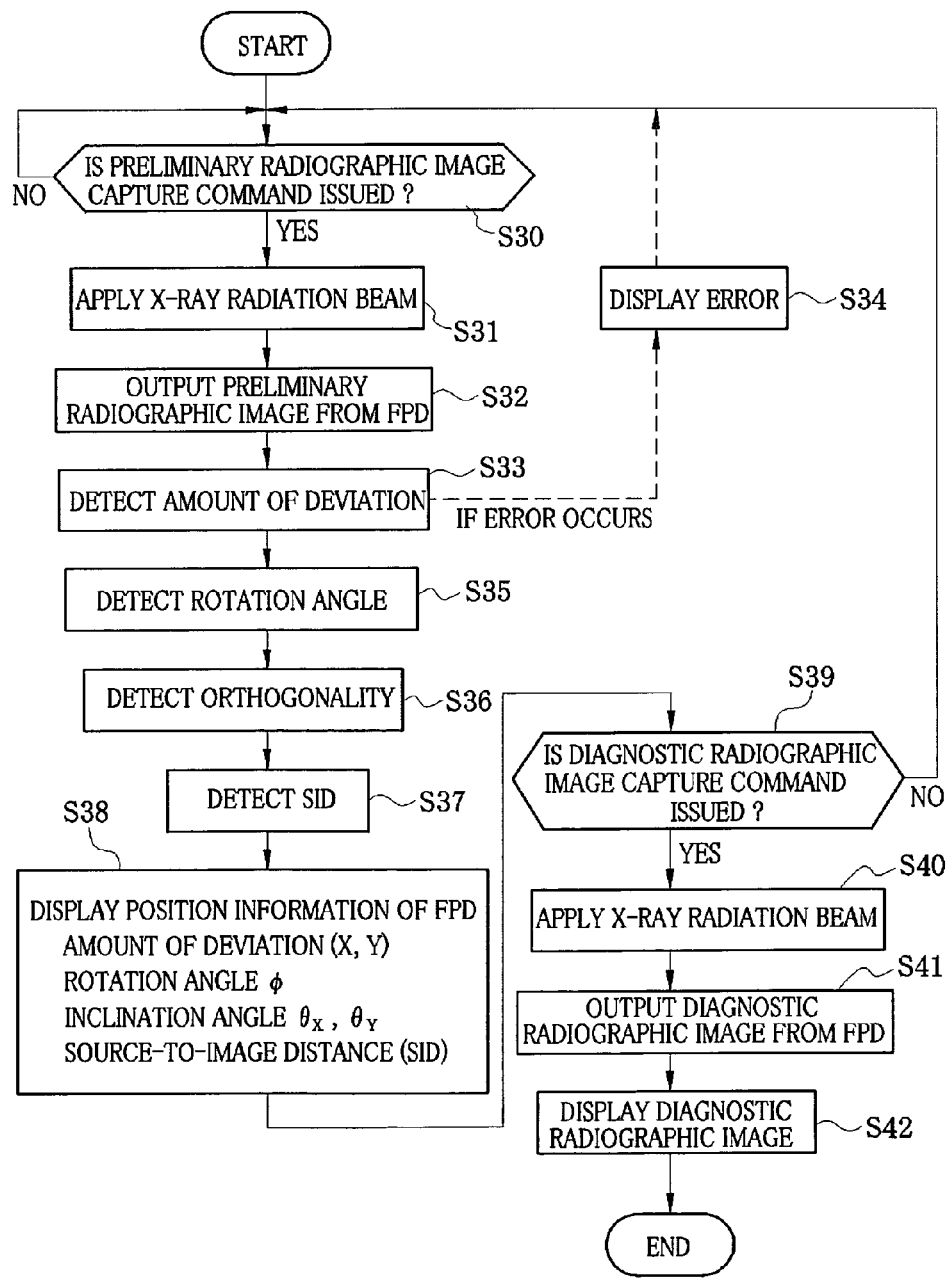
FIG. 10 is a flowchart of the operation of the X-ray imaging device.

Next, the operation of the X-ray imaging device 10 will be described with referring to a flowchart of FIG. 10. To check the position of the FPD 12 relative to the X-ray generator 11, the preliminary radiographic image capture command is issued from the operation command input section 22 (YES in S30) in a state of the filter plate 20 being fitted into the filter attachment section 16a, and then the controller 21 starts controlling the operation of each part.

The high voltage generator 23 firstly applies voltage lower than that for capturing the diagnostic radiographic image to the X-ray tube 15. The X-ray tube 15 generates the X-ray radiation beam with intensity lower than that for capturing the diagnostic radiographic image. The X-ray radiation beam is partly cut out by the collimator unit 16 so as to have the rectangular X-ray field 11a. The X-ray radiation beam passes through the markers M0 to M3 of the filter plate 20 fitted into the filter attachment section 16a and the body part of the patient, and forms the marker images N0 to N3 corresponding to the markers M0 to M3 on the imaging surface 12a of the FPD 12 (S31). As described above, since the X-ray radiation beam applied in capturing the preliminary radiographic image has the intensity lower than that in capturing the diagnostic radiographic image, it is possible to reduce unnecessary radiation absorption by the patient.

Then, the FPD 12 outputs image data (S32). The image data is written as the preliminary radiographic image to the image memory 24 in the main body 13 through the cable 13b. Then, the deviation vector detector 25 carries out the processing shown by the flowchart of FIG. 4, in order to calculate the amount of deviation (X, Y) of the center Q of the imaging surface 12a with respect to the center P of the X-ray field 11a (S33).

In S33, if the error is outputted (S12 of FIG. 4) because the plurality of marker images having different sizes are undetectable, an error message, which describes that the center P of the X-ray field 11a is undetectable due to too large deviation of the FPD 12, is displayed on the monitor 14 (S34), and the operation returns to S30. After the position of the FPD 12 is adjusted in response to the error message, the preliminary radiographic image capture command is inputted again.

Then, the rotation angle detector 26 calculates the rotation angle φ of the imaging surface 12a around the central ray C of the X-ray radiation beam (S35). The orthogonality detector 27 calculates the inclination angles $\theta_X$ and $\theta_Y$ of the imaging surface 12a in the X and Y directions orthogonal to the central ray C (S36). The SID detector 28 calculates the SID from the X-ray focus F to the center P of the X-ray field 11a (S37).

Position information of the FPD 12 calculated in S33, S35 to S37 that includes the amount of deviation (X, Y), the rotation angle φ, the inclination angles $\theta_X$ and $\theta_Y$, and the SID are displayed on the monitor 14 (S38). Based on the position information, the position of the FPD 12 is precisely adjustable. After that, the preliminary radiographic image is re-captured, or the diagnostic radiographic image is captured. Before the capture of the diagnostic radiographic image, the filter plate 20 must be detached from the filter attachment section 16a.

The controller 21 judges which of the preliminary radiographic image capture command and the diagnostic radiographic image capture command is inputted from the operation command input section 22 (S39). If the preliminary radiographic image capture command is inputted (N0 in S39), the operation of S30 to S38 are repeated. If the diagnostic radiographic image capture command is inputted (YES in S39), the high voltage generator 23 applies high voltage to the X-ray tube 15, so that the X-ray tube 15 generates the X-ray radiation beam with intensity higher than that for capturing the preliminary radiographic image. The X-ray radiation beam is partly cut out by the collimator unit 16 so as to have the rectangular X-ray field 11a. The X-ray radiation beam passes through the body part of the patient, and is incident upon the imaging surface 12a of the FPD 12 (S40). The FPD 12 produces image data from the incident X-ray radiation beam, and writes the image data as the diagnostic radiographic image to the image memory 24 (S41). The diagnostic radiographic image is displayed on the monitor 14 (S42).

In the first embodiment, the ratio of size between the pair of adjoining markers varies from pair to pair, for the purpose of distinguishing to which of the markers M0 to M3 the marker image pair extracted from the preliminary radiographic image correspond, with use of the size of each marker as a characteristic value. Instead of the size of the marker, the shape of the marker may vary as the characteristic value.

Figure 11:
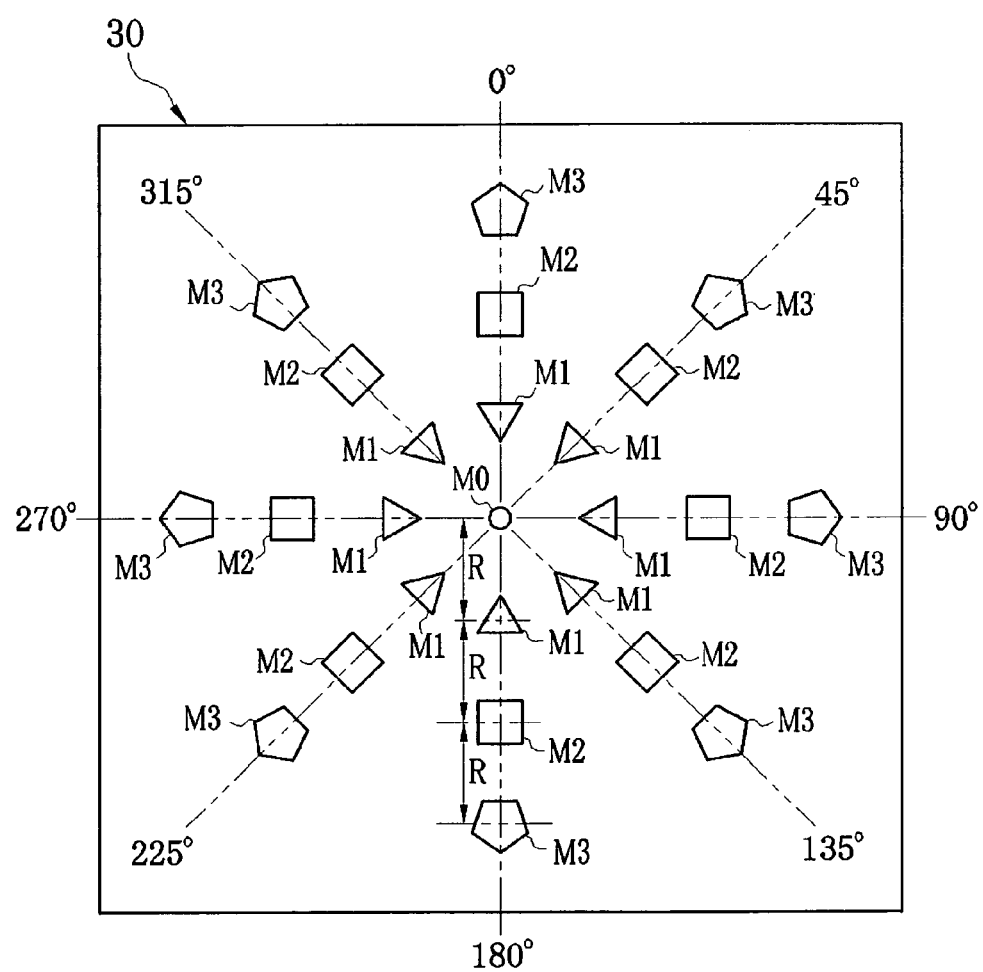
FIG. 11 is a top plan view of a filter plate of another example.

FIG. 11 shows another example of a filter plate that uses the shapes of the markers as the characteristic values. In a filter plate 30, the marker M0 is a circular hole. The markers M1 are regular triangular holes. The markers M2 are square holes, and the markers M3 are regular pentagonal holes. The layout of the markers M0 to M3 is same as that of the filter plate 20. The markers M1 to M3 are disposed on each line that radiates from the marker M0 with forming 0°, 45°, 90°, 135°, 180°, 225°, 270°, or 315° with the vertical center line of the filter plate 30 on one-by-one basis. The shapes and layout of the markers M0 to M3 are stored in advance on the ROM of the controller 21. In using this filter plate 30, the deviation vector detector 25 chooses a pair of marker images that have different shapes from each other and the shortest center-to-center distance, from the preliminary radiographic image. The deviation vector detector 25 identifies the direction of the central marker image, which corresponds to the marker M0, from a line connecting the centers of the chosen marker image pair. Then, distance to the central marker image is determined from the shape of the marker image, and hence the position of the central marker image, that is, the center P of the X-ray field 11a is detected. The orthogonality detector 27 calculates the inclination angles $\theta_X$ and $\theta_Y$ of the imaging surface 12a based on the shape of the marker image. The other structure is same as above.

Figure 12:
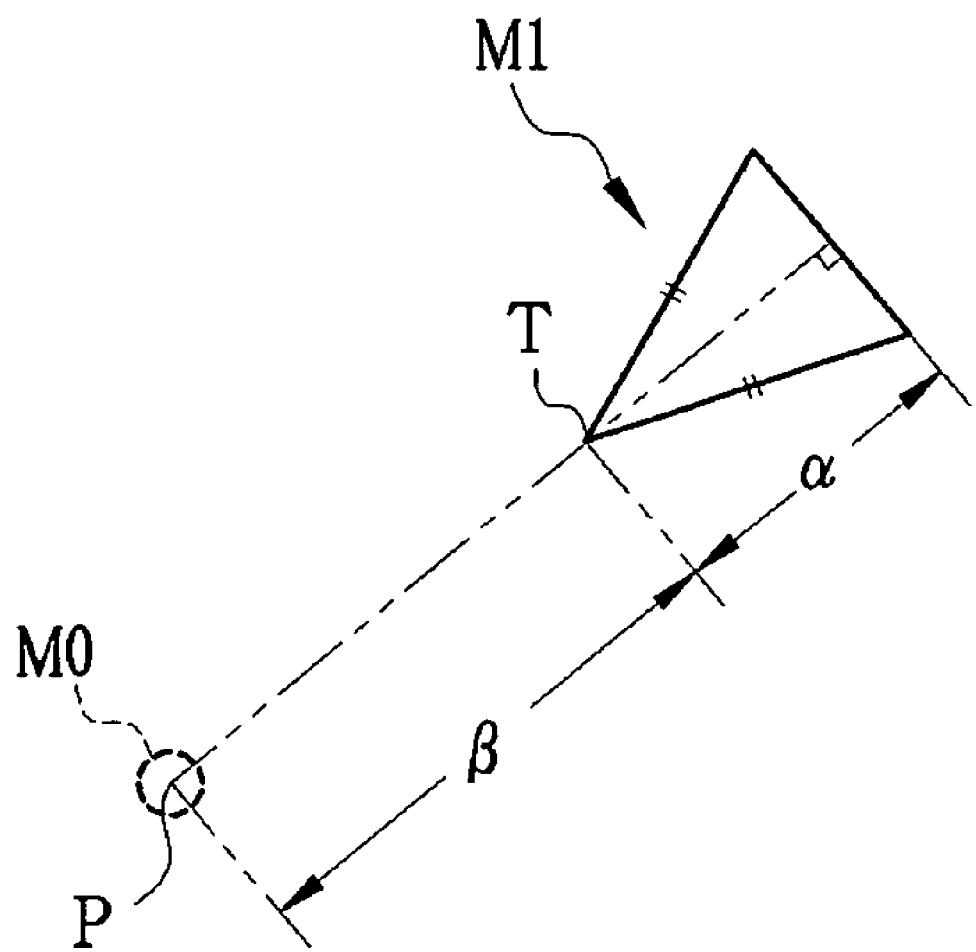
FIG. 12 is an explanatory view showing a marker of further another example and how to calculate the center of the X-ray field from the shape of the marker.

In the case of varying the shapes of markers as the characteristic values, two marker images are not always necessary to identify the center P of the X-ray field 11a, and the single marker image may be adequate. In this case, as shown in FIG. 12, a marker M1 is formed in the shape of an isosceles triangle, and the marker M1 is disposed so that a vertex T is pointed at a marker M0 formed at the center of a filter plate. Thus, a central marker image corresponding to the marker M0 is positioned on a straight line that is orthogonal to the base of the isosceles triangle and through the vertex T of a marker image corresponding to the marker M1. The ratio between a height α of the isosceles triangle and a distance β from the vertex T to the center of the marker M0 is stored in advance on the ROM of the controller 21. Thus, the position of the central marker image, that is, the center P of the X-ray field 11a is determined from the height (the number of pixels) of the isosceles triangle of the marker image, a pixel pitch, and the ratio between the height α and the distance β stored in advance.

In the first embodiment, the filter plate 20 has to be manually fitted into the filter attachment section 16a before capturing the preliminary radiographic image, and the filter plate 20 has to be manually detached therefrom before capturing the diagnostic radiographic image. Therefore, the attachment or the detachment of the filter plate 20 may be sometimes forgotten. In order to prevent this, it is preferable that a sensor be provided to detect a state of filter attachment, and the preliminary radiographic image or the diagnostic radiographic image be captured in accordance with the detected state.

Second Embodiment

In an X-ray imaging device according to a second embodiment, the markers M0 to M3 are formed in the collimator leaves, in order to produce the preliminary radiographic image without using the filter plate 20 or 30. The X-ray imaging device according to the second embodiment has the same structure as that of the X-ray imaging device 10 according to the first embodiment, except for the collimator leaves.

Figure 13:
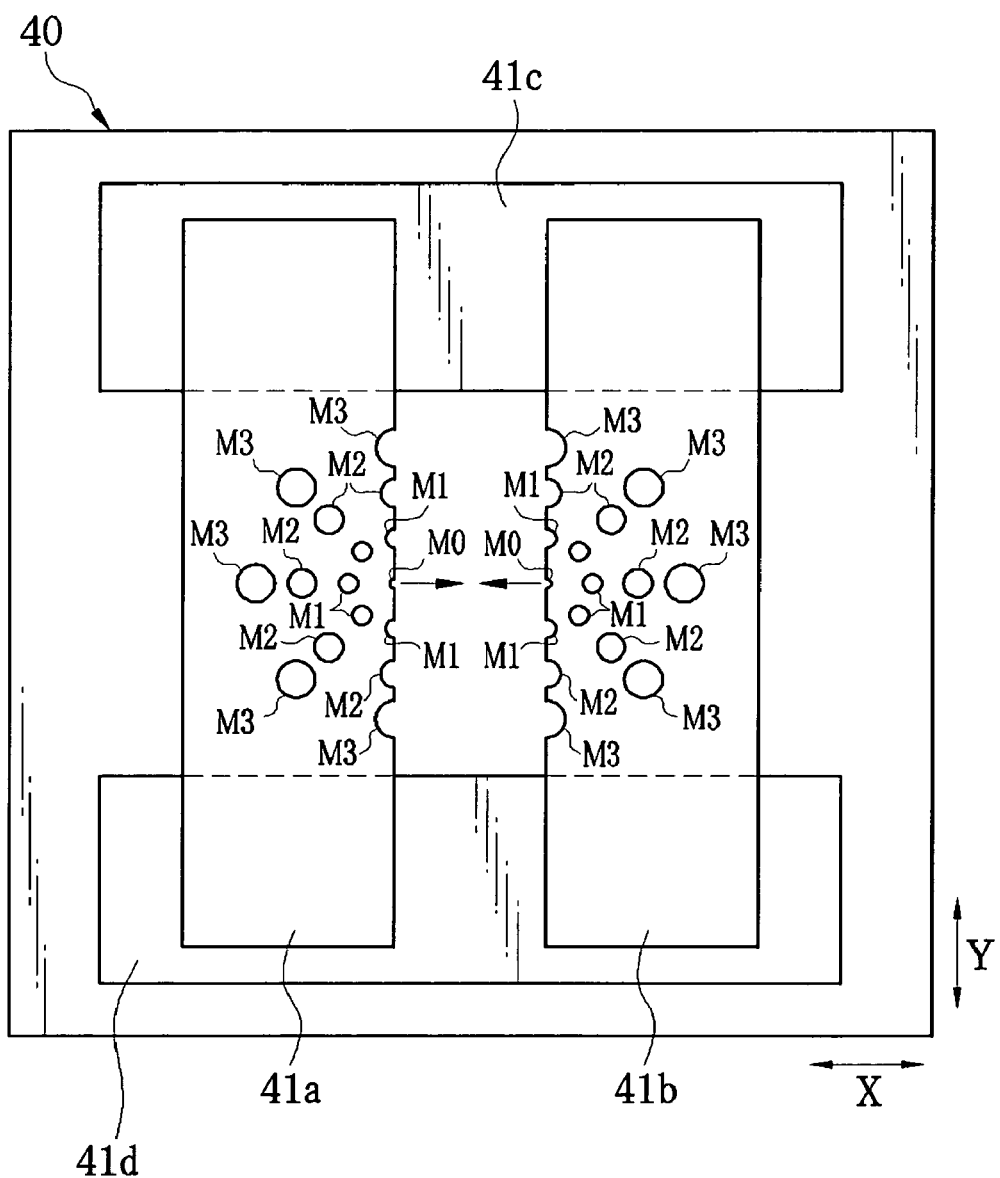
FIG. 13 is a bottom plan view of a collimator unit according to a second embodiment.

As shown in FIG. 13, a collimator unit 40 according to the second embodiment is provided with first and second collimator leaves 41a and 41b that are openable and closable in the X direction, and third and fourth collimator leaves 41c and 41d that are openable and closable in the Y direction. In the first and second collimator leaves 41a and 41b, circular holes are formed as the markers M0 to M3. By closing the first and second collimator leaves 41a and 41b, the markers M0 to M3, which are in the same layout as those of the filter plate 20 shown in FIG. 3, appear in the first and second collimator leaves 41a and 41b.

The controller 21 controls the opening and closing operation of the first to fourth collimator leaves 41a to 41d. In capturing the preliminary radiographic image, the first and second collimator leaves 41a and 41b are closed at a midpoint in the X direction, while the third and fourth collimator leaves 41c and 41d are still opened in the Y direction. Thus, the X-ray radiation beam is mostly cut off by the first and second collimator leaves 41a and 41b, and passes through only the markers M0 to M3. Therefore, an image similar to that of the first embodiment is formed on the imaging surface 12a of the FPD 12. Methods for detecting the amount of deviation (X, Y), the rotation angle φ, the inclination angles $\theta_X$ and $\theta_Y$, and the SID are same as those of the first embodiment, and description thereof will be omitted.

In capture of the diagnostic radiographic image, the first and second collimator leaves 41a and 41b are opened, and the first to fourth collimator leaves 41a to 41d forms the rectangular X-ray field 11a. Since the markers M0 to M3 are formed in the first and second collimator leaves 41a and 41b, the X-ray radiation beam that has passed through the markers M0 to M3 is incident upon the body part of the patient. However, minimizing the sizes of the markers M0 to M3 allows reduction of the unnecessary radiation absorption by the body part of the patient as low as possible.

According to the X-ray imaging device of the second embodiment, as described above, it is unnecessary to attach or detach the filter plate. Automatically controlling the operation of the collimator leaves 41a to 41d in response to the preliminary or diagnostic radiographic image capture command can prevent the occurrence of a human error, e.g. to forget about attaching or detaching the filter plate, and loss and damage of the filter plate.

Third Embodiment

In the X-ray imaging devices according to the first and second embodiments, the holes of the markers M0 and M3 are formed in the filter plate or the collimator leaves, and the preliminary radiographic image is produced from the X-ray radiation beam that has passed through the markers M0 to M3. In contrast, an X-ray imaging device according to a third embodiment produces the preliminary radiographic image in which X-ray density is reduced in stages from center to edge, with use of a filter plate that has different X-ray transmittance from area to area.

Figure 14:
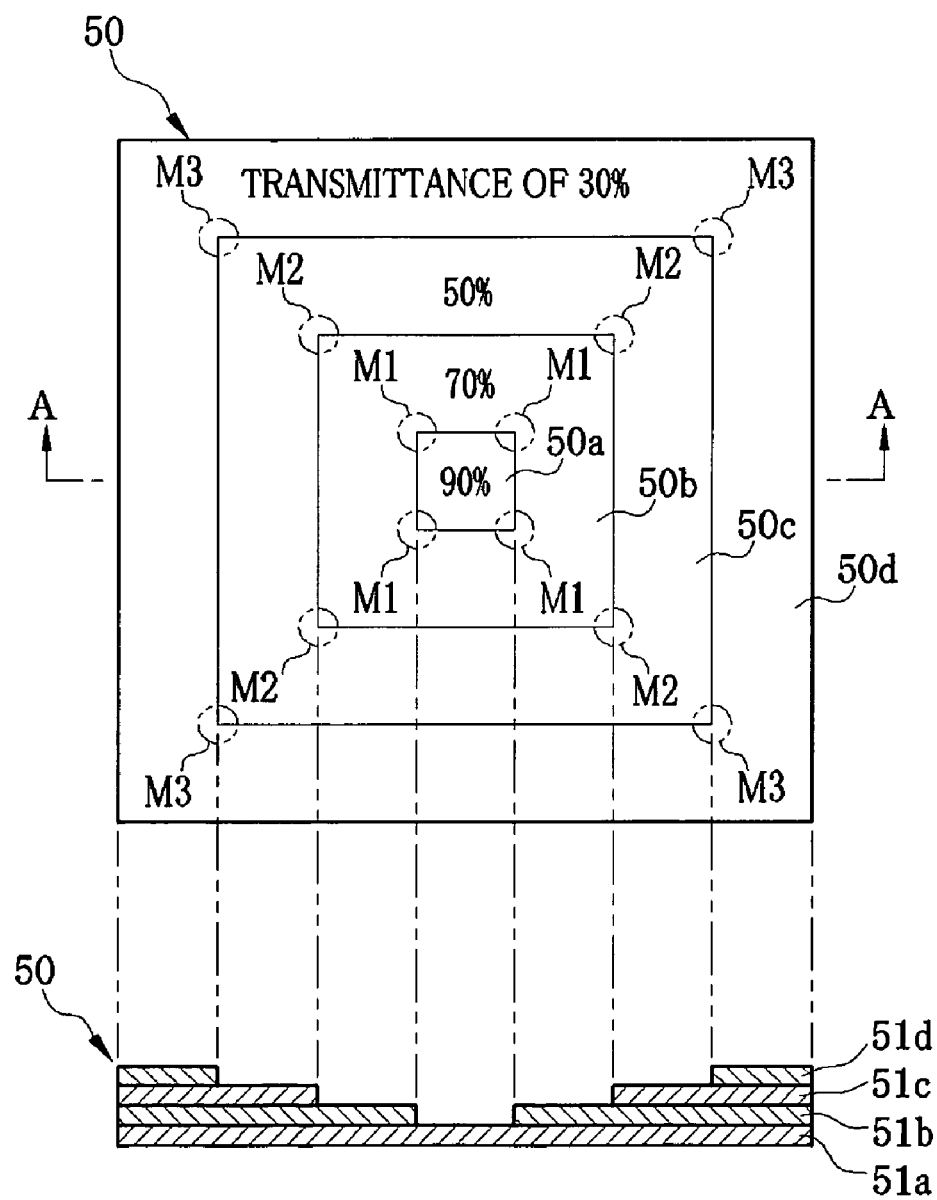
FIG. 14 is a top plan view of a filter plate according to a third embodiment and a cross-sectional view thereof taken along line A-A.

In FIG. 14, a filter plate 50 of the third embodiment is divided into first to fourth areas 50a to 50d that have different X-ray transmittance. The square first area 50a disposed at the center of the filter plate 50 has transmittance of approximately 90%. The square frame-shaped second area 50b surrounding the first area 50a has transmittance of approximately 70%. The square frame-shaped third area 50c surrounding the second area 50b has transmittance of approximately 50%. The square frame-shaped fourth area 50d surrounding the third area 50c has transmittance of approximately 30%.

As shown in FIG. 14, the filter plate 50 is composed of lamination of first to fourth filter parts 51a to 51d having predetermined transmittance. In the filter plate 50, only the first filter part 51a is present in the first area 50a, and the first and second filter parts 51a and 51b are present in the second area 50b. The first to third filter parts 51a to 51c are present in the third area 50c, and the first to fourth filter parts 51a to 51d are present in the fourth area 50d. The thicknesses and material of the first to fourth filter parts 51a to 51d are appropriately adjusted so that the first to fourth areas 50a to 50d have the above transmittance.

With use of the filter plate 50, the FPD 12 captures the preliminary radiographic image that has the different X-ray density from area to area, in accordance with the X-ray transmittance of the first to fourth areas 50a to 50d. In this filter plate 50, the corners of the first to third areas 50a to 50c function as the markers M1 to M3, and the X-ray transmittance (X-ray density) of each area functions as the characteristic value of each marker. Since the markers M1 to M3 are disposed on the lines radiating from the center of the filter plate 50, the position of the center P of the X-ray field 11a is determined by extrapolation, as in the case of the first embodiment.

The outside shapes of the first to fourth areas 50a to 50d are not limited to the square, but may be a regular polygon such as a hexagon or an octagon.

In this third embodiment, the preliminary radiographic image in which the X-ray density varies in stages from center to edge is produced with use of the filter plate 50. The similar preliminary radiographic image may be produced without using the filter plate 50, by means of the collimator leaves varying the size of the X-ray field in stages, and the X-ray generator 11 varying the intensity of the X-ray radiation beam. In this case, a conventional collimator unit is available.

As described above, in the X-ray imaging device 10 having the separate X-ray generator 11 and FPD 12 each of which relative position is unfixed, it is possible to precisely detect the positional deviation of the FPD 12 relative to the X-ray generator 11, even if the deviation is large.

In the X-ray imaging device according to the first to third embodiments, the detected position information of the FPD 12 is displayed on the monitor 14, and the position of the FPD 12 is manually adjusted based on the displayed information. Instead of the manual adjustment, the FPD 12 or the X-ray generator 11 may be provided with a shift mechanism to automatically move the FPD 12 or the X-ray generator 11 in accordance with the detected position information of the FPD 12. If the FPD 12 is attached to an upright stand, for example, the upright stand may be provided with an FPD shift mechanism for shifting the FPD 12 in accordance with the position information. The upright stand may contain the deviation vector detector 25, the rotation angle detector 26, and the orthogonality detector 27.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:
1. An X-ray imaging device comprising:
an X-ray generator for applying an X-ray radiation beam to an object to be viewed;
a position detection pattern disposed between the X-ray generator and the object to be viewed, for partly passing the X-ray radiation beam therethrough;
a flat panel detector disposed behind the object to be viewed, for producing a preliminary radiographic image from the X-ray radiation beam having passed through the position detection pattern and the object to be viewed and being incident upon an imaging surface of the flat panel detector; and
a deviation vector detector for determining a center of an X-ray field of the X-ray radiation beam from the preliminary radiographic image, and for calculating a deviation vector extending from the center of the X-ray field to a center of the imaging surface of the flat panel detector.

2. The X-ray imaging device according to claim 1, wherein the position detection pattern includes a plurality of markers, and the markers are laid out in such a manner that marker images formed by the X-ray radiation beam having passed through the markers are disposed radially from the center of the X-ray field in the preliminary radiographic image.

3. The X-ray imaging device according to claim 2, wherein the markers are laid out on the position detection pattern in such a manner that the marker images having different characteristic values are disposed radially from the center of the X-ray field, and the marker images having the same characteristic value are disposed at a same distance from the center of the X-ray field, and the deviation vector detector determines the center of the X-ray field from two of the marker images having the different characteristic values and a shortest center-to-center distance.

4. The X-ray imaging device according to claim 2, wherein the position detection pattern is a filter plate having holes as the markers, and the filter plate is detachably attached to an X-ray outlet of the X-ray generator.

5. The X-ray imaging device according to claim 2, wherein the position detection pattern is a collimator leaf having holes as the markers.

6. The X-ray imaging device according to claim 3, wherein the markers have a circular shape, and the characteristic value of each marker image is a size of the marker image, and the deviation vector detector determines the center of the X-ray field based on a ratio in size between the two marker images adjoining to each other.

7. The X-ray imaging device according to claim 3, wherein the markers have various polygonal shapes, and the characteristic value of each marker image is a shape of the marker image, and the deviation vector detector determines the center of the X-ray field based on the shapes of the two marker images adjoining to each other.

8. The X-ray imaging device according to claim 2, further comprising:
a rotation angle detector for detecting a rotation angle of the imaging surface of the flat panel detector relative to the X-ray field of the X-ray radiation beam, from the center of the X-ray field determined by the deviation vector detector and the single marker image, or from the two marker images.

9. The X-ray imaging device according to claim 2, further comprising:
an orthogonality detector for detecting orthogonality of the imaging surface of the flat panel detector relative to a central ray of the X-ray radiation beam, on the basis of difference in shape between the single marker and the marker image corresponding to the single marker.

10. The X-ray imaging device according to claim 2, further comprising:
a source-to-image distance detector for detecting a source-to-image distance from an X-ray focus of the X-ray generator to the imaging surface of the flat panel detector, on the basis of a ratio in size between the single marker and the marker image corresponding to the single marker.

11. The X-ray imaging device according to claim 2, wherein the position detection pattern is a filter plate having a plurality of areas of different X-ray transmittances as the markers, and the filter plate is detachably attached to an X-ray outlet of the X-ray generator, and a plurality of marker images produced from the X-ray radiation beam having passed through the areas have X-ray densities different from one another as characteristic values, and the deviation vector detector determines the center of the X-ray field on the basis of a ratio in the X-ray density between two of the marker images.

12. The X-ray imaging device according to claim 1, wherein the position detection pattern is an openable and closable collimator leaf, and the preliminary radiographic image is obtained with a software program for synchronously controlling intensity of the X-ray radiation beam emitted from the X-ray generator and a degree of opening of the collimator leaf.

13. The X-ray imaging device according to claim 1, wherein in capturing the preliminary radiographic image, the X-ray generator is supplied with a voltage lower than that in capturing a diagnostic radiographic image, so as to generate the X-ray radiation beam of intensity lower than that in capturing the diagnostic radiographic image.

14. A method for detecting a deviation of a flat panel detector comprising the steps of:
generating an X-ray radiation beam of low intensity from an X-ray generator;
passing the X-ray radiation beam through a position detection pattern and an object to be viewed, and applying the passed X-ray radiation beam to an imaging surface of a flat panel detector;
generating a preliminary radiographic image from the applied X-ray radiation beam;
determining a center of an X-ray field of the X-ray radiation beam from the preliminary radiographic image; and
calculating a deviation vector extending from the center of the X-ray field to a center of the imaging surface of the flat panel detector.

15. The method according to claim 14, wherein the center of the X-ray field of the X-ray radiation beam is determined by extrapolation.

16. The method according to claim 15, further comprising at least one of the steps of:
detecting a rotation angle of the imaging surface of the flat panel detector relative to the X-ray field of the X-ray radiation beam from the preliminary radiographic image;
detecting orthogonality of the imaging surface of the flat panel detector relative to a central ray of X-ray radiation beam from the preliminary radiographic image; and
detecting a source-to-image distance from an X-ray focus of the X-ray generator to the imaging surface of the flat panel detector from the preliminary radiographic image.

17. The method according to claim 16, further comprising the step of:
displaying on a monitor at least one of the deviation vector, the rotation angle, the orthogonality, and the source-to-image distance detected from the preliminary radiographic image.

18. A non-transitory computer readable storage medium having stored thereon a computer program executable to perform the steps of:
generating an X-ray radiation beam of low intensity from an X-ray generator;
passing the X-ray radiation beam through a position detection pattern and an object to be viewed, and applying the passed X-ray radiation beam to an imaging surface of a flat panel detector;
generating a preliminary radiographic image from the applied X-ray radiation beam;
determining a center of an X-ray field of the X-ray radiation beam from the preliminary radiographic image; and
calculating a deviation vector extending from the center of the X-ray field to a center of the imaging surface of the flat panel detector.

* * * * *